United States Patent
Gray et al.

(10) Patent No.: US 12,251,535 B2
(45) Date of Patent: Mar. 18, 2025

(54) FLUID PUMP NOTIFICATION AND CONTROL BASED ON MONITORED FEEDBACK

(71) Applicant: Ivenix, Inc., North Andover, MA (US)

(72) Inventors: George W. Gray, North Andover, MA (US); Jesse E. Ambrosina, Topsfield, MA (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 766 days.

(21) Appl. No.: 17/231,840

(22) Filed: Apr. 15, 2021

(65) Prior Publication Data
US 2021/0322675 A1    Oct. 21, 2021

Related U.S. Application Data

(60) Provisional application No. 63/012,399, filed on Apr. 20, 2020.

(51) Int. Cl.
*A61M 5/172* (2006.01)
*A61M 5/142* (2006.01)

(52) U.S. Cl.
CPC .......... *A61M 5/1723* (2013.01); *A61M 5/142* (2013.01); *A61M 2005/14208* (2013.01);
(Continued)

(58) Field of Classification Search
CPC .......... A61M 2005/14208; A61M 2005/1726; A61M 2205/18; A61M 2205/33;
(Continued)

(56) References Cited

U.S. PATENT DOCUMENTS

| | | |
|---|---|---|
| 5,256,157 A | 10/1993 | Samiotes et al. |
| 7,220,240 B2 | 5/2007 | Struys et al. |
| | (Continued) | |

FOREIGN PATENT DOCUMENTS

| | | |
|---|---|---|
| AU | 2013206325 A1 | 7/2013 |
| CA | 2129227 A1 | 8/1993 |
| | (Continued) | |

OTHER PUBLICATIONS

Pajic, et al, "Model-Driven Safety Analysis of Closed-Loop Medical Systems", IEEE Transactions on Industrial Informatics 10(1), 3-16. Jan. 2011, pp. 1-12.
(Continued)

*Primary Examiner* — Shefali D Patel
(74) *Attorney, Agent, or Firm* — Armis IP Law, LLC

(57) ABSTRACT

A fluid delivery system includes a fluid pump and a fluid management system. The fluid management system receives input indicating a fluid (such as including a drug, a therapy, etc.) of a particular type to be delivered to a recipient. The fluid management system maps the particular type of the fluid to a set of patient parameters to be monitored during the delivery of the fluid to the recipient. During the delivery of the fluid to the recipient, the fluid management system monitors feedback from the recipient for each of the patient parameters in the set. Based on the feedback, the fluid management system controls the delivery of the fluid to the recipient.

22 Claims, 11 Drawing Sheets

(52) U.S. Cl.
CPC ..... *A61M 2205/18* (2013.01); *A61M 2205/33* (2013.01); *A61M 2205/3327* (2013.01); *A61M 2205/50* (2013.01); *A61M 2205/52* (2013.01); *A61M 2230/04* (2013.01); *A61M 2230/201* (2013.01); *A61M 2230/40* (2013.01)

(58) Field of Classification Search
CPC ...... A61M 2205/3327; A61M 2205/50; A61M 2205/52; A61M 2230/005; A61M 2230/04; A61M 2230/06; A61M 2230/20; A61M 2230/201205; A61M 2230/30; A61M 2230/40; A61M 2230/42; A61M 5/14; A61M 5/142; A61M 5/168; A61M 5/16804; A61M 5/16831; A61M 5/1677; A61M 5/172; A61M 5/1723
See application file for complete search history.

(56) References Cited

U.S. PATENT DOCUMENTS

| | | |
|---|---|---|
| 8,271,106 B2 | 9/2012 | Wehba et al. |
| 8,518,021 B2 | 8/2013 | Stewart et al. |
| 9,682,193 B2 | 6/2017 | Anand et al. |
| 9,934,540 B2 | 4/2018 | Schneider et al. |
| 10,064,579 B2 | 9/2018 | Condurso et al. |
| 10,478,558 B2 | 11/2019 | Uram et al. |
| 10,549,036 B2 | 2/2020 | Starkweather et al. |
| 2005/0234432 A1 | 10/2005 | Stein |
| 2006/0047538 A1 | 3/2006 | Condurso et al. |
| 2012/0310152 A1 | 12/2012 | Wehba et al. |
| 2017/0165412 A1 | 6/2017 | Kelly et al. |
| 2017/0189654 A1 | 7/2017 | Schwartz et al. |
| 2017/0372441 A1* | 12/2017 | Adams .................. G16H 40/20 |
| 2018/0085055 A1 | 3/2018 | Annoni et al. |
| 2018/0169332 A1 | 6/2018 | Sadeghzadeh et al. |
| 2019/0001039 A1 | 1/2019 | Heide et al. |
| 2019/0131009 A1 | 5/2019 | Som et al. |

FOREIGN PATENT DOCUMENTS

| | | |
|---|---|---|
| CN | 1901954 A | 1/2007 |
| CN | 201049109 Y | 4/2008 |
| CN | 101961519 A | 2/2011 |
| CN | 203736613 U | 7/2014 |
| CN | 106334231 A | 1/2017 |
| CN | 107111856 A | 8/2017 |
| WO | 2007147505 A2 | 12/2007 |
| WO | 2014159280 A1 | 10/2014 |

OTHER PUBLICATIONS

International Search Report, PCT/US2021/027502, Aug. 5, 2021, pp. 1-2.

Supplementary European Search Report, EP 21 79 3457, Apr. 25, 2024, pp. 1-10.

* cited by examiner

MAP INFO.
<u>150</u>

| <u>FLUID TYPE</u> | <u>ALGORITHM</u> | <u>PARAMETER(S)</u> |
|---|---|---|
| FLUID TYPE #1 | 170-1 | P1, P5 |
| FLUID TYPE #2C | 170-2 | P2, P5 |
| FLUID TYPE #3 | 170-3 | P2, P3 |

FLUID PUMP NOTIFICATION AND CONTROL BASED ON MONITORED FEEDBACK

RELATED APPLICATION

This application claims the benefit of earlier filed U.S. Patent Application Ser. No. 63/012,399 entitled "FLUID PUMP CONTROL BASED ON MONITORED FEEDBACK," filed on Apr. 20, 2020, the entire teachings of which are incorporated herein by this reference.

BACKGROUND

A conventional process of delivering fluid-based drugs requires multiple operations by a respective caregiver. For example, a physician must first generate a medication order specifying one or more fluid-based drugs for delivery to a particular patient in a hospital. Typically, a pharmacy in the hospital receives the medication order supplied by the physician. In accordance with the medication order, the pharmacy dispenses a corresponding physical order by providing the drugs to a caregiver for delivery to a respective patient.

Infusion devices deliver medications and other solutions that affect the physiology of the patient. On a regular basis, a caregiver must manually assess, via network in-person visit, the physiology of a patient via review of vital signs, lab results, clinical assessments and other observations collected by medical devices and/or recorded within the electronic medical record (EMR). Clinicians typically review these observations prior to the administration of medications and other solutions to ensure that the proposed infusion therapy will be effective and not have an adverse effect on the patient's condition.

BRIEF DESCRIPTION OF EMBODIMENTS

Conventional techniques of intravenously delivering fluid to a patient suffer from deficiencies. For example, operations of managing delivery of one or more fluids to a patient is tedious and can result in fluid delivery errors. In some instances, clinical information associated with the patient is sometimes overlooked or is not readily available to a clinician, putting the recipient at risk of receiving a particular drug.

In contrast to conventional techniques, embodiments herein include a fluid pump and fluid management system. The fluid management system receives input indicating a fluid (such as a drug or other therapy) of a particular type to be delivered to a recipient. The fluid management system maps the particular type of the fluid to a set of parameters to be monitored during delivery of the fluid to the recipient. During delivery of the particular fluid to the recipient, the fluid management system monitors feedback from the recipient for each of the parameters in the set. Based at least in part on the feedback, the fluid management system controls delivery of the fluid from the fluid pump to the recipient.

Note that the set of parameters (such as patient parameters) include any suitable information. For example, in one embodiment, the set of parameters to be monitored are pertinent to delivery of the fluid and possible adverse effects to the recipient based on a history of delivering the particular type of fluid to other patients who had adverse effects.

In accordance with further example embodiments, the set of patient parameters monitored via the feedback include assessments and/or other clinical observations included in the recipient's record of care.

Further embodiments herein, via the fluid management system, include configuring a fluid delivery algorithm of the fluid pump to monitor the feedback from the multiple monitored patient parameters in the set and executing the fluid delivery algorithm at the fluid pump contingent on the feedback. In further example embodiments, the executed fluid delivery algorithm oversees delivery of the fluid to the recipient.

Note that the fluid management system as discussed herein can support any operations during delivery or setup of delivering the particular fluid to the recipient. For example, in one embodiment, the fluid management system alerts a respective caregiver during programming of the fluid pump regarding the set of patient parameters to be monitored during delivery of the particular fluid (i.e., fluid of a particular type) to the recipient. If desired, the respective caregiver can adjust the parameters and/or corresponding settings of the parameters to be monitored.

In still further example embodiments, controlling delivery of the particular type of fluid to the recipient includes providing alerts and/or discontinuing delivery of the fluid to the recipient in response to detecting an adverse impact to the recipient caused by the fluid delivery as indicated by the feedback. Accordingly, embodiments herein include modifying a routine of delivering the particular type of fluid to the recipient based on comparison of the feedback to corresponding one or more parameters (such as threshold value settings in the set.

Additionally, or alternatively, note that the fluid delivery system can be configured to generate an alarm during the delivery of the particular fluid by the fluid pump in response to detecting a condition associated with the fluid delivery as indicated by the feedback.

Further, the parameters in the set as monitored by the fluid delivery system can vary depending on the embodiment. For example, in one embodiment, the set of parameters monitored via the feedback include lab results associated with the recipient.

In accordance with another example embodiment, the set of patient parameters monitored via the feedback include vital signs of the recipient such as one or more of the following: i) heart rate, ii) blood pressure, iii) respiration rate, iv) blood oxygen saturation level, v) blood glucose levels, vi) partial thromboplastin time test, etc.

Note further that the parameters to monitor during delivery of the particular type of fluid therapy can be determined in any suitable manner. For example, in one embodiment, the set of parameters pertinent to delivery of the particular type of fluid (such as drug, therapy, etc.) are learned from monitoring delivery of the particular type of fluid to a population of multiple patients and determining the reactions of the population to receiving same. Additionally, or alternatively, the parameters to be monitored during a respective infusion can be determined based on determining which patient parameters are most likely to be impacted adversely based on the delivery of the particular type of fluid.

Additionally, or alternatively, the parameter to be monitored can be associated with an expected update frequency such as when the fluid delivery system should receive new sample data for the one or more monitored parameters. If new data samples are not received within a defined window at or around the expected update frequency the fluid delivery system can generate an alarm to notify the clinician that the expected data from the monitor equipment was not received by the fluid delivery system. In such an instance, the alert to the caregiver can indicate that the algorithm is no longer able to perform its intended function because no sample data of monitored parameters is being received.

These and other more specific embodiments are disclosed in more detail below.

Note that any of the resources as discussed herein can include one or more computerized devices, fluid delivery systems, servers, base stations, wireless communication equipment, communication management systems, workstations, handheld or laptop computers, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (i.e., any physical computer readable hardware storage medium) on which software instructions are encoded for subsequent execution. The instructions, when executed in a computerized device (e.g., computer processing hardware) having a processor, program and/or cause the processor to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, etc., or other a medium such as firmware, in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment herein includes a computer readable storage medium and/or system having instructions stored thereon. The instructions, when executed by computer processor hardware, cause the computer processor hardware to: receive input indicating a fluid of a particular type to be delivered to a recipient; map the particular type of the fluid to a set of parameters; during delivery of the particular type of fluid to the recipient, monitor feedback from the recipient for each of the parameters in the set; and control delivery of the fluid from a fluid pump to the recipient based on the feedback.

The ordering of the operations above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or within a software application.

As discussed herein, techniques herein are well suited for managing and facilitating use of medical devices. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

BRIEF DESCRIPTION OF THE DRAWINGS

FIG. 3 is an example diagram illustrating a mapping of fluid drug type to a delivery algorithm and corresponding set of one or more delivery parameters according to embodiments herein.

Figure 1:
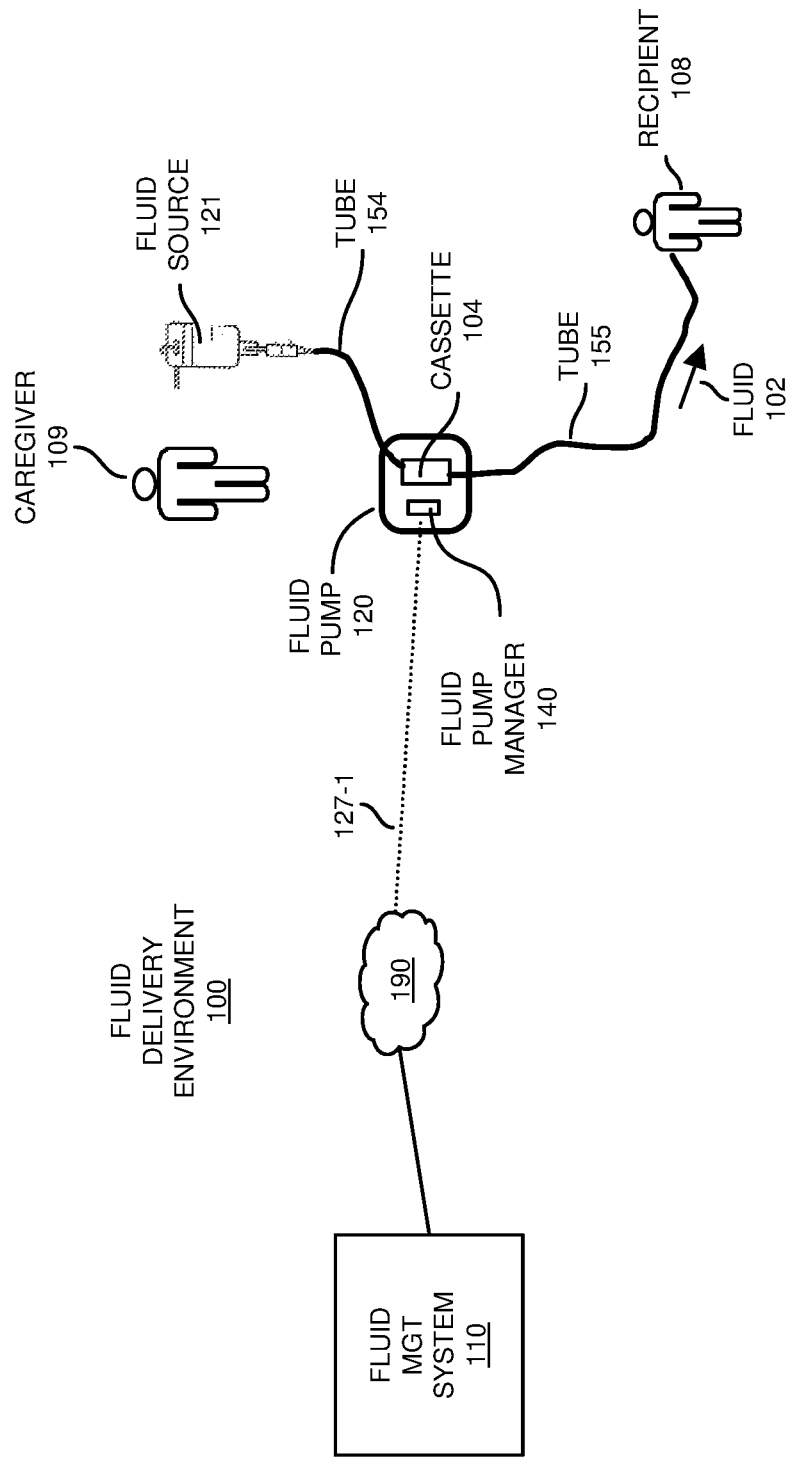
FIG. 1 is an example diagram illustrating a fluid delivery system according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

A fluid delivery system includes a fluid pump and a fluid management system. The fluid management system receives input indicating a fluid of a particular type to be delivered to a recipient. The fluid management system maps the particular type of the fluid to a set of parameters to be monitored during delivery of the fluid to the recipient. During delivery of the particular fluid to the recipient, the fluid management system monitors feedback from the recipient for each of the one or more patient parameters in the set. Based on the feedback, the fluid management system provides alerts and/or controls delivery of the fluid to the recipient.

Now, more specifically, FIG. 1 is an example diagram illustrating a fluid delivery system according to embodiments herein.

As shown, the fluid delivery environment 100 includes fluid management system 110, network 190, and fluid pump 120. Fluid pump 120 includes disposable cassette 104 and fluid pump manager 140 (controller). Disposable cassette 104 includes appropriate mechanical components, electrical components, etc., to control a rate of delivering fluid 102 through the tube 155 to the recipient in accordance with a fluid delivery order and input from the caregiver 109.

Fluid pump manager 140 of the fluid pump 120 and/or fluid management system 110 controls delivery of a respective fluid (such as fluid therapy) to a recipient 108 in accordance with input from the fluid management system 110 and/or caregiver 109.

More specifically, caregiver 109 oversees operation of the fluid pump 120 to deliver the fluid 102 (stored in the fluid source 121) to the recipient 108 (such as patient). For example, the caregiver 109 provides connectivity of the fluid source 121 (storing respective fluid 102) to the fluid pump 120 via tube 154. The caregiver 109 further provides connectivity of the fluid pump 120 to the recipient 108 via tube 155.

Wireless or wired communication link 127-1 and network 190 provide communication connectivity between the fluid pump 120 and the fluid management system 110.

Note that any of the resources as discussed herein can be implemented via hardware, software, or a combination of hardware and software. For example, the fluid pump manager 140 can be configured as fluid pump manager hardware, fluid pump manager software, or a combination of fluid pump manager hardware and fluid pump manager software; the fluid management system 110 can be configured as fluid management hardware, fluid manager software, or a combination of fluid manager hardware and fluid manager software; and so on.

Figure 2:
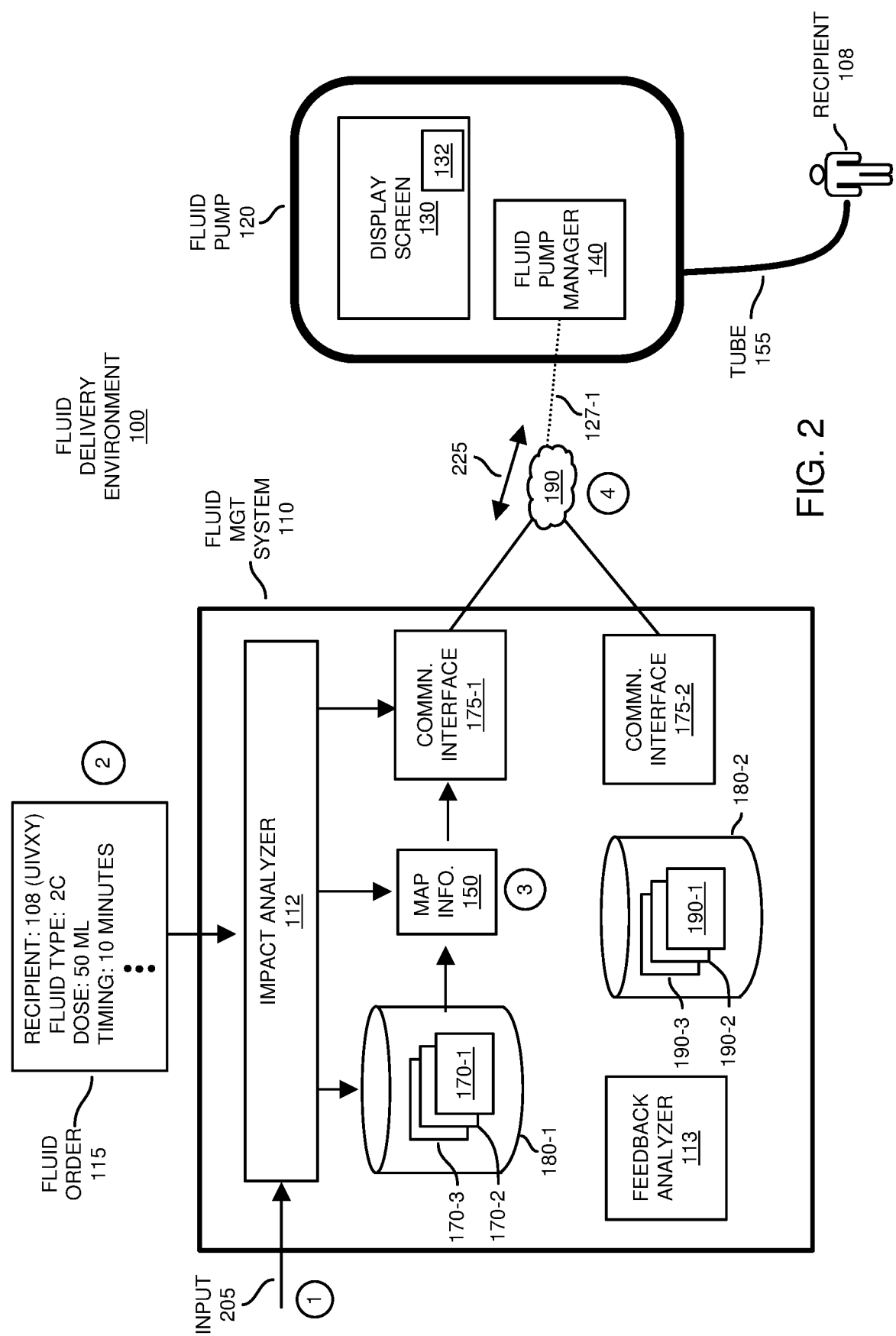
FIG. 2 is an example diagram illustrating determination of an appropriate algorithm to monitor fluid delivery according to embodiments herein.

FIG. 2 is an example diagram illustrating management of delivering fluid therapy according to embodiments herein.

As previously discussed, and as more particularly shown in FIG. 2, the fluid delivery environment 100 includes a fluid management system 110 and fluid pump 120. Fluid pump 120 delivers selected fluid (such as fluid 102) to recipient 108 via tube 155.

Embodiments herein include keeping track of one or more patient parameters that pertain to delivery of fluid to recipients.

For example, in processing operation #1, the impact analyzer 112 of the fluid management system 110 receives input 205 indicating which of multiple parameters (such as vital signs or other suitable parameters indicating a health of a patient) pertain to delivery of different types of fluid therapies such as drugs.

In one embodiment, it is desirable to monitor different patient parameters (such as one or more of heart rate, body temperature, blood pressure, respiration rate, blood oxygen saturation level, blood glucose levels, partial thromboplastin time test, cardiac output level, etc.) depending upon the type of fluid being delivered to the recipient 108.

Map information 150 indicates different types of patient parameters most pertinent to the delivery of a corresponding fluid.

FIG. 3 is an example diagram illustrating a mapping of drug type to a delivery algorithm and corresponding set of one or more delivery parameters according to embodiments herein.

For example, in one embodiment as shown in FIG. 3, the map information 150 indicates that parameters P1 and P5 are to be monitored during delivery of fluid type #1 to a respective recipient. Additionally, map information 150 indicates a corresponding algorithm 170-1 pertinent to delivering the fluid type #1. In this example embodiment, assume that the algorithm 170-1 indicates or includes threshold information associated with the selected parameters P1 and P5. The algorithm 170-1 is operative to monitor received feedback associated with fluid delivery and initiate generation of an alert on the display screen 130 (or audible alert from a speaker) of the fluid pump 120 to caregiver 109 in response to detecting a condition in which the monitored feedback for the one or more parameters fall outside a desired range as further discussed herein during a corresponding fluid delivery to the recipient 108.

As further shown, the map information 150 indicates that parameters P2 and P5 are to be monitored during delivery of fluid type #2C to a respective recipient. Additionally, map information 150 indicates a corresponding algorithm 170-2 pertinent to delivering the fluid type #2 (such as Heparin). In this example embodiment, the algorithm 170-2 indicates or includes threshold information associated with the selected parameters P2 and P5.

As further discussed herein, the algorithm 170-2 can be configured to monitor received feedback associated with fluid delivery and initiate generation of an alert on the display screen 130 to caregiver 109 in response to detecting a condition in which the monitored feedback for one or more parameters fall outside a desired range during a corresponding fluid 102 delivery to the recipient 108.

The map information 150 indicates that parameters P2 and P3 are to be monitored during delivery of fluid type #3 to a respective recipient. Additionally, map information 150 indicates a corresponding algorithm 170-3 pertinent to delivering the fluid type #3 (such as Morphine). In this example embodiment, assume that the algorithm 170-3 indicates or includes threshold information associated with the selected parameters P2 and P3. As further discussed herein, the algorithm 170-3 can be configured to monitor received feedback associated with fluid delivery and initiate generation of an alert on the display screen 130 to caregiver 109 in response to detecting a condition in which the monitored feedback for one or more parameters fall outside a desired range during a corresponding fluid delivery to the recipient.

Referring to FIG. 3 and again to FIG. 2, in further example embodiments, any suitable entity creates the input 205 and corresponding map information 150 based on prior experiences (history) of delivering the different types of fluids to recipients. Additionally, or alternatively, in one embodiment, the input 205 is based on medical analysis of which of multiple parameters are most important to monitor during a respective type of fluid infusion.

Thus, via map information 150, the fluid management system 110 maps the particular type of the drug (fluid) as specified by the order 115 to a set of patient parameters to be monitored during delivery of the drug to the recipient 108.

In one nonlimiting example embodiment, the fluid type #1 maps to parameters P1 (respiration rate) and P5 (heart rate); fluid type 2C maps to parameters P2 (such as blood oxygen saturation level) and P5 (heart rate); fluid type #3 maps to P2 (blood oxygen level) and P3 (blood pressure); and so on.

Note that the set of patient parameters associated with each fluid therapy includes any suitable information. For example, in one embodiment, the set of patient parameters are pertinent to delivery of the respective fluid therapy such as drug and possible or likely adverse effects to the recipient based on a history of delivering the respective type of drug to other patients.

Note further that the parameters to monitor during delivery of a respective particular type of drug can be determined in any suitable manner. For example, in one embodiment, the set of parameters pertinent to delivery of the particular type of drug are learned from monitoring delivery of the respective type of drug to a population of multiple patients and their reactions to same.

Additionally, or alternatively, as previously discussed, the parameters to be monitored for a given infusion can be determined based on a theoretical study of patient parameters P1, P2, P3, etc., that are most likely to be impacted during delivery of the respective type of drug.

Note further that the parameters monitored by the respective algorithm can vary depending on the embodiment. For example, in one embodiment, the set of patient parameters monitored via the feedback include lab results associated with the recipient 108. In accordance with another example embodiment, the set of patient parameters monitored via the feedback include vital signs of the recipient such as one or more of the following: i) P1—respiration rate, ii) P2—blood oxygen level, iii) P3—blood pressure, iv) P4—blood glucose levels, v) P5—heart rate, vi) P6—partial thromboplastin time test, etc.

In processing operation #2 of FIG. 2, the impact analyzer 112 receives or retrieves further input indicating a fluid order 115 prescribed by a caregiver such as a doctor to the recipient 108.

The fluid order 115 (such as drug order, therapy order, etc.) includes any suitable information.

For example, in one embodiment, the fluid order 115 indicates an identity (such as name assigned or unique identifier value UIVXY) of the recipient 108 to which the fluid order 115 pertains.

Additionally, the fluid order 115 indicates a particular type of fluid 102 (such as a drug of a particular type 2C) to be delivered from the fluid pump 120 through the tube 155 to the recipient 108.

In certain instances, the fluid order 115 includes or specifies delivery instructions such as a rate and/or amount of fluid to be delivered to the recipient 108.

In further example embodiments, the fluid management system 110 communicates the fluid order 115 over network 190 and communication link 127-1 to the fluid pump manager 140 of the fluid pump 120. The fluid pump manager 140 initiates display of notification 132 on the display screen 130 of fluid pump 120. The notification 132 indicates useful information such as the fluid order 115 and guides the respective caregiver 109 in a delivery and setup of the fluid pump 120 to deliver fluid 102 (such as a particular type of fluid 2C as indicated by the fluid order) to the recipient 108.

In addition to providing notification of the fluid order 115 to the fluid pump manager 140, in processing operation #3, the impact analyzer 112 of the fluid management system 110 analyzes the fluid order 115 to determine one or more parameters that pertain to delivery of the respective fluid order 115 to the recipient 108.

As previously discussed, the repository 180-1 stores algorithms 170 (such as algorithm 170-1, algorithm 170-2, algorithm 170-3, etc.) associated with different types of fluid that can be delivered to a respective recipient. In this example embodiment, the impact analyzer 112 uses the map information 150 to map the fluid order 115 (and fluid type 2C) to algorithm 170-2 and corresponding parameters P2 and P5 to be monitored while delivering the fluid 102 (type 2C) to the recipient 108. As previously discussed, the selected algorithm 170-2 includes any suitable information facilitating delivery of the fluid as specified by the fluid order 115 to recipient 108.

In processing operation #4, the fluid management system 110 communicates the selected algorithm 170-2, and/or parameters P2 and P5, etc., to the fluid pump 120 and/or feedback analyzer 113 of fluid management system 110. The selected algorithm 170-2 is configured to monitor the feedback for the multiple patient parameters P2 and P5 during delivery of drug #2C (fluid) to the recipient 108 via tube 155.

Figure 4:
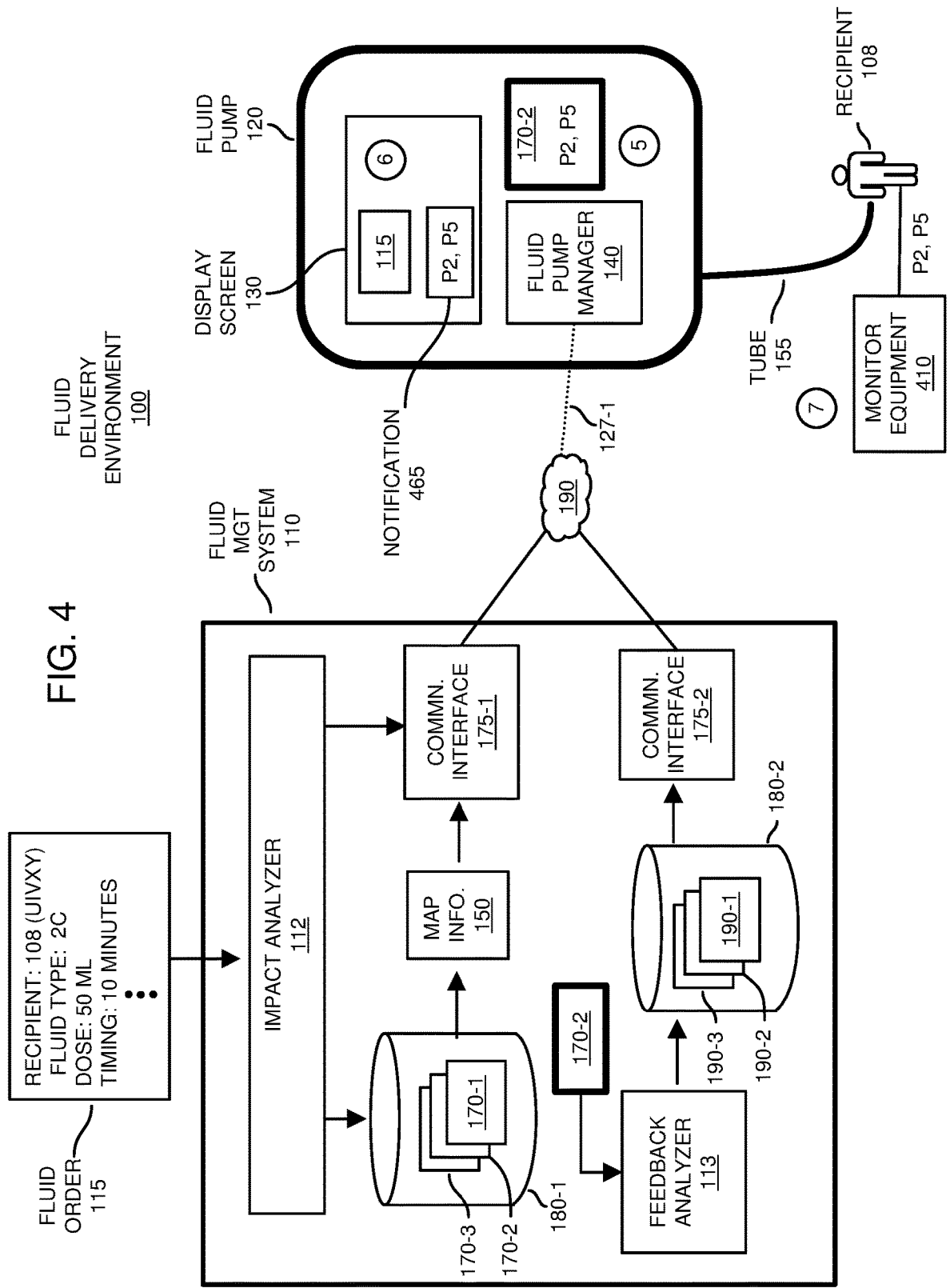
FIG. 4 is an example diagram illustrating notification of one or more parameters to monitor while delivering a respective fluid to a recipient according to embodiments herein.

FIG. 4 is an example diagram illustrating notification of one or more parameters to monitor while delivering a respective fluid to a recipient according to embodiments herein.

In processing operation #5, the fluid pump 120 receives the algorithm 170-2 or at least the notification 465 of parameters P2 and P5 to be monitored during the delivery of the fluid 2C as specified by the fluid order 115 to the recipient 108.

Note again that the selected algorithm 170-2 can be executed at any suitable one or more location such as fluid management system 110, fluid pump 120, etc.

In one embodiment, in processing operation #6, the fluid pump manager 140 initiates display of the parameters P2 and P5 in notification 465 on the display screen 130 for viewing by the caregiver 109. This notifies the caregiver 109 of the relevant parameters to monitor during the infusion as specified by the fluid order 115.

Additionally, the fluid pump manager 140 initiates display of any other information on display screen (or plays back via audio) any guidance associated with infusing the recipient 108 in accordance with the fluid order 115.

Thus, in one embodiment, via information on display screen 130 or other notifications provided by any suitable entity, the fluid management system 110 alerts a respective caregiver 109 during programming of the fluid pump 120 regarding the set of patient parameters (such as via notification 132 on the display screen 130) to be monitored during delivery of the particular drug #2C to the recipient 108. If desired, the respective caregiver 109 can review and/or select the parameters or corresponding settings of the parameters to be monitored via the algorithm 170-2.

In further example embodiments, display of the parameters P2 (such as blood saturation) and P5 (such as heartbeat rate) notifies the respective caregiver 109 of the corresponding type of monitor equipment 410 to retrieve and attach to the recipient 108 for monitoring purposes.

In further example embodiments, display of the parameters P2 (such as blood saturation) and P5 (such as heartbeat rate) includes additional information indicating to the respective caregiver 109 of the expected update frequency for each of the monitored parameters. The update frequency indicates a schedule or timing in the monitor equipment is to provide sample data collected from monitoring each of the parameters P2, P5, etc.

In processing operation #7, the caregiver 109 sets up monitor equipment 410 in which to monitor the identified parameters P2 and P5. For example, in one embodiment, the monitor 410 includes equipment to monitor multiple parameters such as heartbeat rate and blood oxygen saturation level.

In further example embodiments, the caregiver configures the monitor 410, including any associated equipment as necessary, such that the update rate of the monitored parameters is aligned with the expected update frequency for each parameter.

Figure 5:
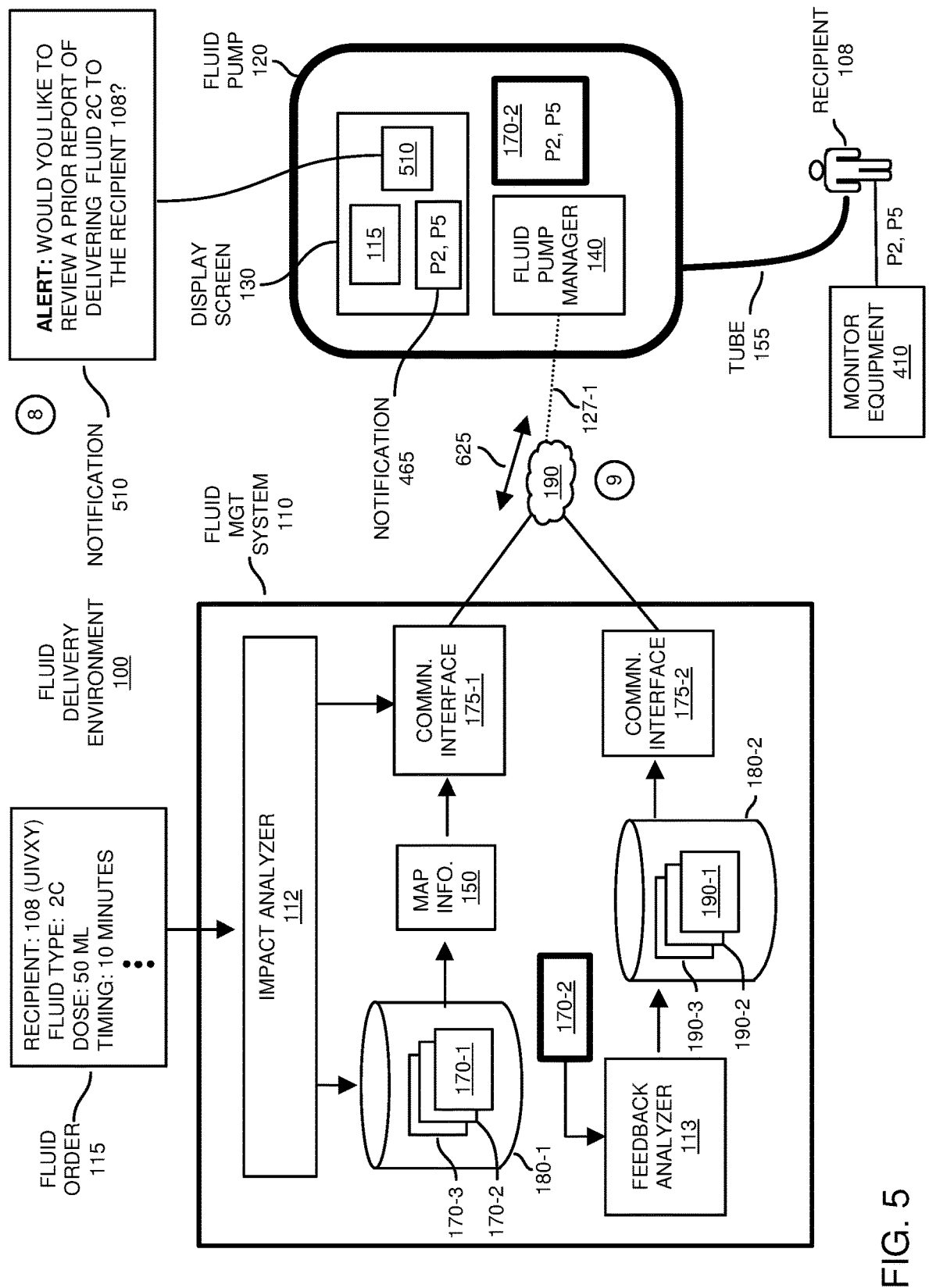
FIG. 5 is an example diagram illustrating notification of availability of a report associated with delivery of a fluid according to embodiments herein.

FIG. 5 is an example diagram illustrating notification of availability of a report associated with delivery of a fluid according to embodiments herein.

In certain instances, it is useful to notify the caregiver 109 of any relevant information associated with delivery of the fluid 102 as specified by the fluid order 115 to the recipient 108.

In further example embodiments, assume that the algorithm 170-2 or other suitable entity detects availability of pertinent medical information associated with the recipient 108 and the delivery of the fluid type 2C to the recipient 108.

In processing operation #8, in response to detecting the availability of pertinent information such as a relevant report associated with the recipient 108 and/or delivery of the fluid 2C, the fluid pump manager 140 displays the notification 510 on the display screen 130. The notification 510 inquires whether the caregiver 109 would like to know of the relevant report. In one embodiment, the relevant report indicates effects on the recipient 108 of infusing the recipient 108 with the fluid #2C or other fluid therapies in the past. This gives the caregiver 109 a sense of what may occur during the present infusion.

In one embodiment, the repository 180-2 stores one or more reports 190 (such as report 190-1, report 190-2, report 190-3, etc.) regarding past delivery of different types of fluids to the recipient 108 and potentially to other recipients. The reports 190 can include any suitable information such as, in one embodiment, prior results (such as report 190-3) of delivering the same fluid (type 2C) or similar therapy to the recipient 108.

If the caregiver 109 responds with a "yes" to notification 510, then the fluid pump manager 140 queries the fluid management system 110 and corresponding repository 180-2 for any pertinent reports of delivering the fluid type #2C or any other type of infusions to the recipient 108. In processing operation #9, via communications 625, the fluid management system 110 communicates report 190-3 to the fluid pump manager 140 for display on the display screen 130. Additionally, or alternatively, the report may be audibly played back to the caregiver 109.

Thus, in one embodiment, the fluid management system 110 such as via executed algorithm 170-2 can be configured to detect relevant report 190-3 for communication to the caregiver 109. Assume that the fluid management system 110 detects that the reports 190 stored in repository 180-2 include a report 190-3 indicating delivery of the fluid 2C to the recipient 108, medical information pertinent to delivery of the fluid order 115 to the recipient, etc.

Via communications 625, the fluid management system 110 communicates the report 190-3 of prior infusion and/or other information relevant to the current infusion over network 190 and communication link 127-1 to the fluid pump manager 140 for display on the display screen 130.

Thus, in one embodiment, via report 190-3, the caregiver 109 can be notified of possible adverse effects (such as indicated by report 190-3) prior to administration of the fluid order 115 to the recipient 108. In view of the report 190-3, the caregiver 109 has an option of terminating delivery of the fluid 2C as specified by the order 115 if the report 190-3 indicates adverse effects on the recipient 108. Alternatively, the report 190-3 may indicate no adverse effects on a prior delivery of the fluid 2C to the recipient 108.

Figure 6:
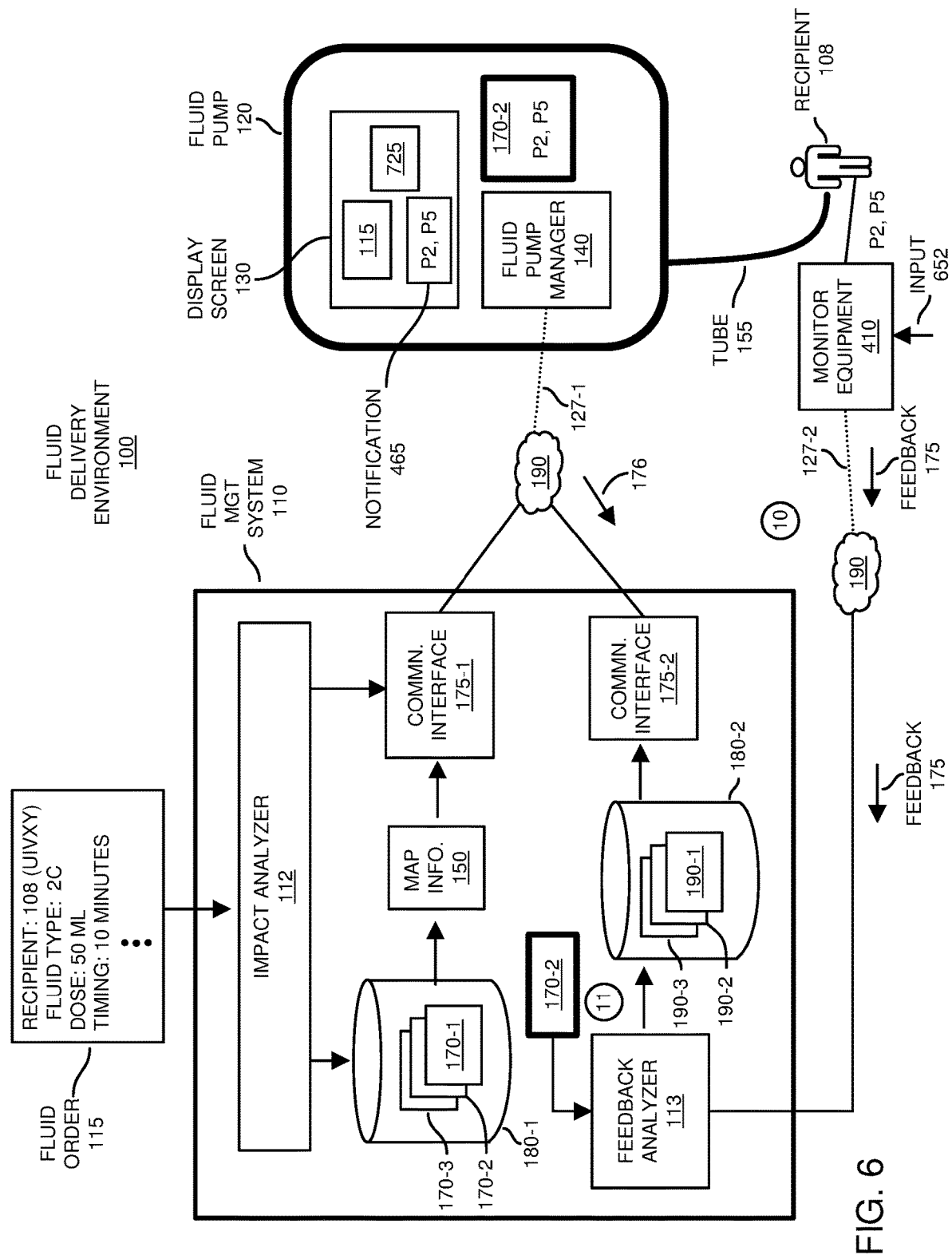
FIG. 6 is an example diagram illustrating monitoring of one or more parameters and providing corresponding feedback according to embodiments herein.

FIG. 6 is an example diagram illustrating monitoring one or more parameters and providing corresponding feedback according to embodiments herein.

As further shown in this example embodiment, the monitor system 410 monitors the parameters P2 and P5 associated with the delivery of fluid 102 of fluid order 115 and communicates corresponding feedback 175 associated with same to the fluid management system 110 and, more specifically, the feedback analyzer 113. The feedback analyzer 113 can be disposed at any suitable location. In one embodiment, as an alternative to being disposed in the fluid management system 110, the feedback analyzer 113 and corresponding functionality is disposed in the fluid pump 120.

If the fluid pump manager 140 executes the algorithm 170-2 (as opposed to the fluid management system 110), the fluid management system 110 forwards the feedback 175 to the fluid pump manager 140 or the monitor equipment 410 can be configured to communicate the feedback 175 directly to the fluid pump manager 140 through the network 190. Thus, the algorithm 170-2 can be executed at any suitable location such as the fluid management system 110, fluid pump 120, etc.

Note that further embodiments herein include the caregiver 109 or other suitable entity supplying appropriate information to the monitor equipment 410 to which the feedback 175 pertains. For example, the caregiver 109 can be configured to provide unique identifier information associated with the fluid pump 120, recipient 180, fluid order 115, etc. The monitor equipment 410 uses the information to tag data associated with monitored parameters to the fluid management system 110. This ensures that the fluid management system 110 is aware of a particular fluid delivery to which the feedback 175 pertains.

In further example embodiments, the feedback analyzer 113 receives the feedback 175 from the monitor equipment 410 prior to start of a respective infusion of the fluid order 115. In response to receiving the feedback 175, and a notification of the current settings of the parameters P2 and P5, the feedback analyzer 113 or other suitable entity communicates a notification to the fluid pump 120 indicating the receipt of the feedback 175 from the monitor equipment 410. The notification from the feedback analyzer 113 indicates (such as on display screen 130, via an audio signal, etc.) that the feedback analyzer 113 currently receives the monitor information produces by the monitor equipment 410 and that the caregiver 109 can start the infusion because the feedback analyzer 113 is receiving the appropriate monitor data from the monitor equipment 410.

In one embodiment, via operation #10, the monitor 410 communicates the feedback 175 (such as heartbeat rate, blood pressure, etc.) over a data stream via network 190 to the feedback analyzer 113 of fluid management system 110.

The data stream includes the feedback 175 as well as information indicating identities such as the recipient 108, fluid order 115, fluid pump 120, etc. The tagging of the feedback 175 with such information (such as unique identifier value UIVXY, identity of recipient 108, etc.) enables the feedback analyzer 113 to generate, as the fluid order 115 is being delivered, an appropriate delivery report for storage in the repository 180-2.

Note that, in further example embodiments, the monitor 410 further communicates time stamp information in or with the feedback 175. The time stamp information indicates one or more different time slots or times to which the corresponding feedback 175 pertains.

In still further example embodiments, the fluid pump manager 140 also communicates feedback 176 to the fluid management system 110 (such as specifically to feedback analyzer 113) during a respective infusion of the fluid type 2C to the recipient 108 as specified by the fluid order 115. As previously discussed, the feedback analyzer 113 of fluid management system 110 or other suitable entity executes the algorithm 170-2 to determine if the infusion (as specified by the fluid order 115) should be terminated or if the caregiver 109 should be alerted based on feedback 175 (such as vital signs) and feedback 176 (such as fluid delivery information).

In yet another example embodiment, the feedback analyzer 113 of fluid management system 110 or other suitable entity executes the algorithm 170-2 to determine if the expected feedback parameter was not received within an expected time window and if the caregiver 109 should be alerted based on lack of feedback 175 (such as vital signs) or lack of feedback 176 (such as fluid delivery information).

Thus, during delivery of the particular fluid (such as type 2C) as specified by the order 115 to the recipient 108, the selected algorithm 170-2 executed by any suitable entity monitors feedback 175 associated with the status of the recipient 108 for each of the patient parameters P2 and P5 in the set as well as feedback 176 associated with the delivery.

In processing operation #11, the feedback analyzer 113 generates a respective report associated with the execution of the fluid order 115 and stores the report in repository 180-2. The report indicates details of the infusion of fluid order 115 such as based on the feedback 175 and the feedback 176.

The newly generated report based on the infusion of fluid order 115 serves as a history of infusing the recipient 108 with the fluid type 2C. This information can be retrieved and reviewed if the caregiver 109 receives a subsequent order to deliver the same fluid therapy (such as fluid type 2C) to the recipient 108. Thus, each generated report potentially serves a basis in which to consider during future infusions to the recipient 108.

Figure 7:
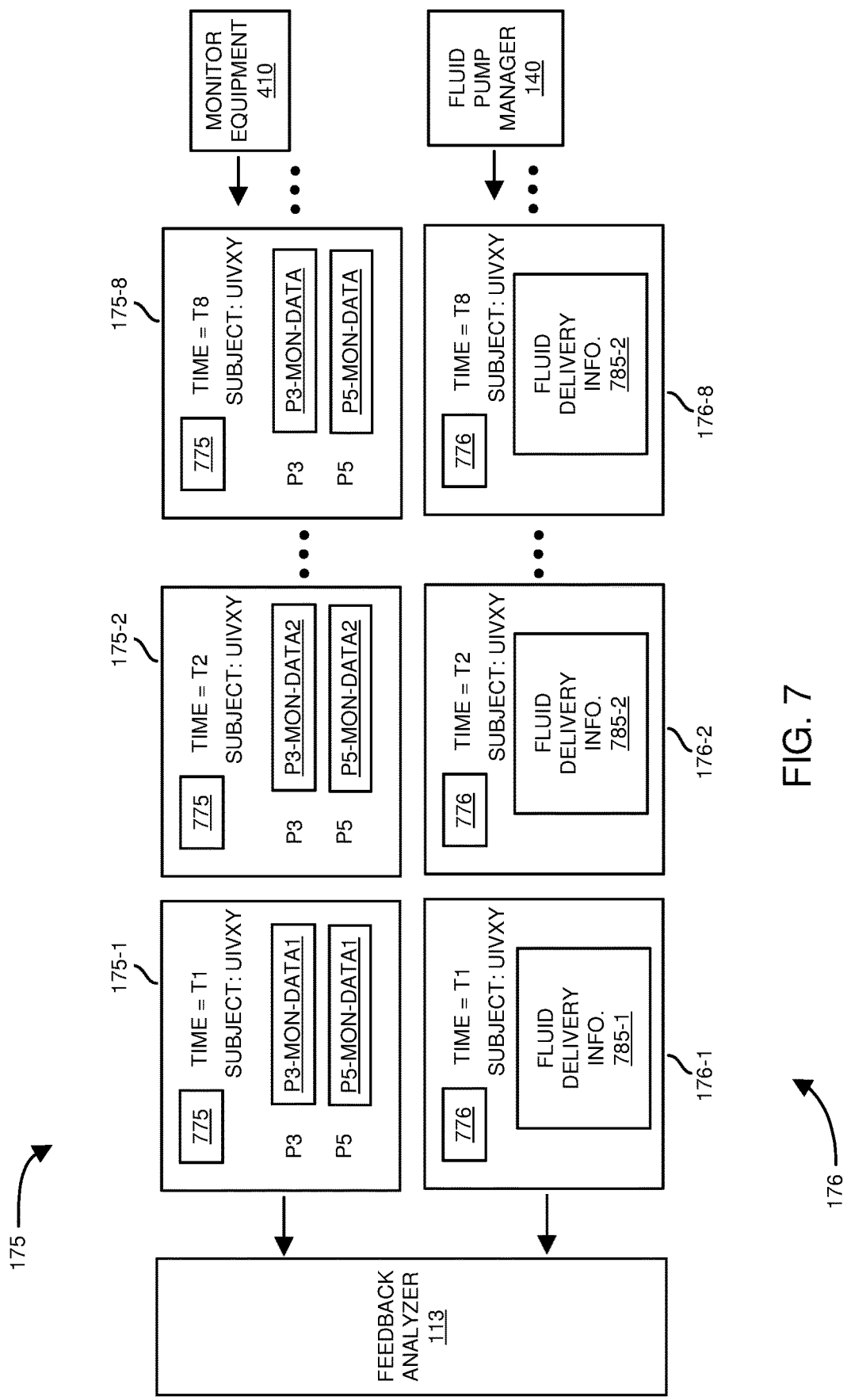
FIG. 7 is an example diagram illustrating receipt and processing of feedback from multiple sources according to embodiments herein.

A further example of communicating feedback data 175 and 176 to the feedback analyzer 113 and controlling operation of or providing notifications (such as alerts) associated with the delivery of the fluid order 115 is shown in FIG. 7.

FIG. 7 is an example diagram illustrating receipt and processing of feedback according to embodiments herein.

In this example embodiment, the monitor equipment 410 communicates the feedback 175 to the feedback analyzer 113. Additionally, the fluid pump manager 140 associated with fluid pump 120 communicates a status of the infusion to the feedback analyzer 113 such as executed by fluid management system 110, fluid pump 120, or other suitable entity.

As shown in this example embodiment, feedback 175 (such as a feedback data stream) includes feedback information 175-1, feedback information 175-2, . . . , feedback information 175-8, and so on. Each of the monitor equipment 410 and the fluid pump manager 140 provide a continuous stream of feedback during the infusion into recipient 108.

In one embodiment, the monitor equipment 410 generates each of the instances of feedback information (such as one or more data packets) to include data such as corresponding monitor data for a given sample period, a unique identifier value UIVXY assigned to the recipient 108 receiving a respective infusion, timing information such as time stamp information indicating a sample period to which the corresponding information pertains, etc. Accordingly, the feedback analyzer 113 is able to match the feedback 175 received from the monitor equipment 410 to the feedback 176 received from the fluid pump manager 140.

As a more specific example, feedback information 175-1 from the monitor equipment 410 includes sample data (such as P2-MON-DATA1, P5-MON-DATA1) associated with each of the respective monitored parameters P2 and P5 assigned for monitoring during the delivery of fluid 102 associated with the fluid order 115. The feedback information 175-1 further includes timing information indicating a time period, time sample, etc., indicating when the data was collected and/or generated by the monitor equipment 410. The data 775 associated with the feedback 175-1 includes any suitable information (such as fluid pump identity, monitor equipment identity, fluid order identity, recipient identity, etc.) indicating that the feedback 175-1 is associated with the infusion of fluid 2C as specified by the fluid order 115.

Feedback information 176-1 from the fluid pump 120 or fluid pump manager 140 includes sample data (such as fluid delivery information 785-1) associated with delivery of fluid 102 to the recipient 108 as specified by the fluid order 115. In one embodiment, the fluid pump 120 keeps track of the amount, rate, etc., of fluid 102 (fluid type 2C) delivered to the recipient 108 over time; the fluid delivery information 785-1 indicates data such as the amount, rate, etc., of fluid 102 (fluid type 2C) delivered to the recipient 108 for a particular time slot. In further example embodiments, the feedback information 176-1 further includes timing information indicating a time period, time sample, etc., indicating when the data was collected and/or generated by the fluid pump 120. The feedback information 176-1 includes any suitable information 776 (such as fluid pump identity, monitor equipment identity, fluid order identity, recipient identity, etc.) indicating that the fluid delivery information 785-1 is associated with the infusion of fluid 2C as specified by the fluid order 115.

Feedback information 175-2 from the monitor equipment 410 includes sample data (such as P2-MON-DATA2, P5-MON-DATA2) associated with each of the respective monitored parameters P2 and P5 assigned for monitoring during the delivery of fluid 102 associated with the fluid order 115. The feedback information 175-2 further includes timing information indicating a time period, time sample, etc., indicating when the data was collected and/or generated by the monitor equipment 410. The data 775 associated with the feedback 175-2 includes any suitable information (such as fluid pump identity, monitor equipment identity, fluid order identity, recipient identity, etc.) indicating that the feedback information 175-2 is associated with the infusion of fluid 2C as specified by the fluid order 115.

Feedback information 176-2 from the fluid pump 120 or fluid pump manager 140 includes sample data (such as fluid delivery information 785-2) associated with delivery of fluid 102 to the recipient 108 as specified by the fluid order 115. In one embodiment, the fluid pump 120 keeps track of the amount, rate, etc., of fluid 102 (fluid type 2C) delivered to the recipient 108 over time; the fluid delivery information 785-2 indicates data such as the amount, rate, etc., of fluid 102 (fluid type 2C) delivered to the recipient 108. In further example embodiments, the feedback information 176-2 further includes timing information indicating a time period, time sample, etc., indicating when the data was collected and/or generated by the fluid pump 120. Via information 776, the feedback information 176-2 includes any suitable information (such as fluid pump identity, monitor equipment identity, fluid order identity, recipient identity, etc.) indicating that the fluid delivery information 785-2 is associated with the infusion of fluid 2C as specified by the fluid order 115.

Figure 8:
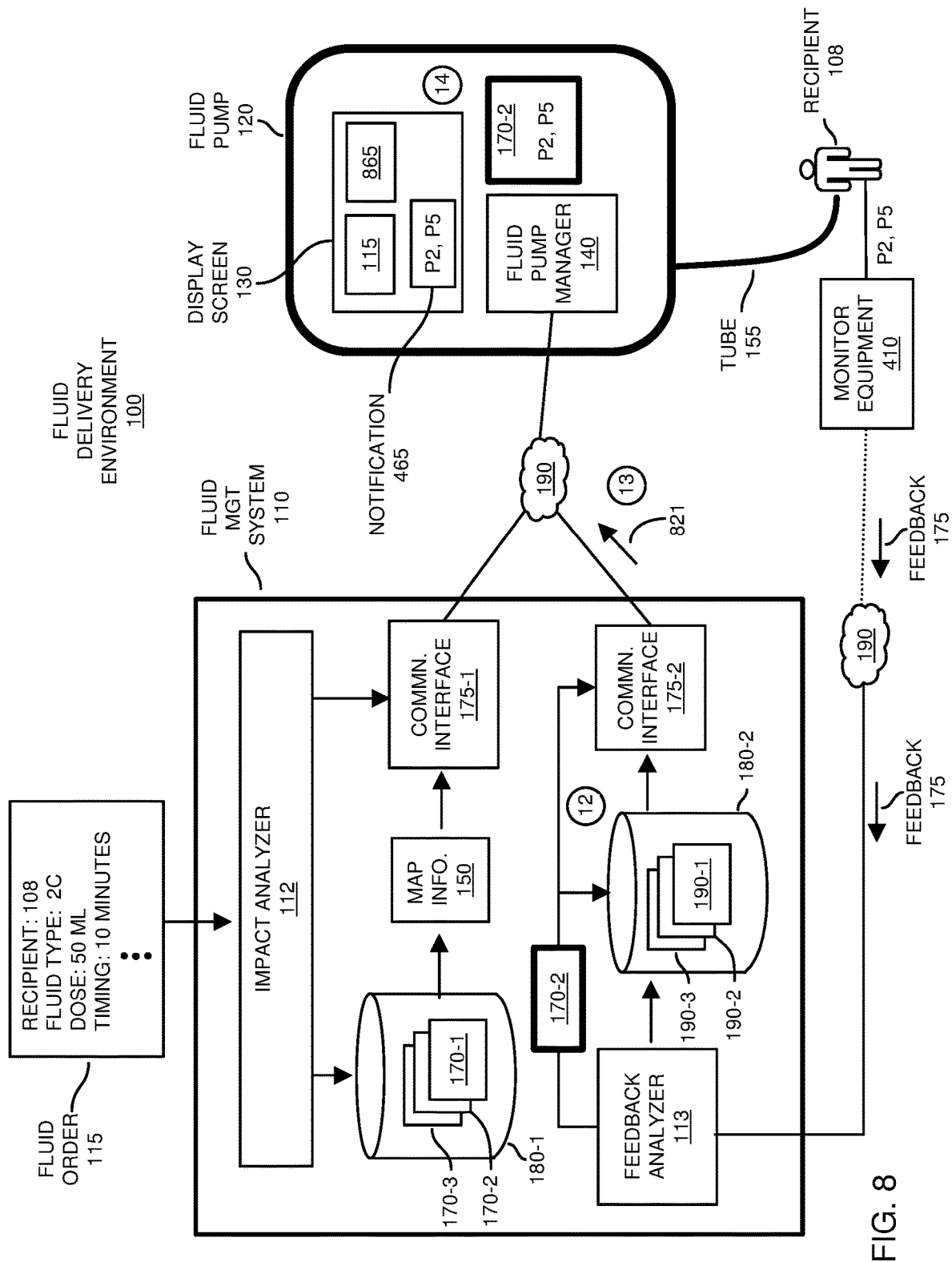
FIG. 8 is an example diagram illustrating generation of a fluid delivery report based on feedback and generation of an alert notification associated with the fluid delivery according to embodiments herein.

FIG. 8 is an example diagram illustrating generation of a fluid delivery report based on feedback and generation of an alert notification associated with the fluid delivery according to embodiments herein.

As previously discussed, based on the feedback 175, via the feedback analyzer 113 and execution of the algorithm 170-2, the fluid management system 110 provides notifications and/or control associated with delivery of the fluid order 115 from the fluid pump 120 to the recipient 108.

For example, as previously discussed, the feedback analyzer 113 executing the algorithm 170-2 can be configured to communicate one or more alerts to a caregiver 109 depending on the feedback 175.

In yet further example embodiments, controlling delivery of the fluid 102 associated with fluid order 115 to the recipient via the algorithm 171 includes discontinuing delivery of the fluid 102 to the recipient (such as patient) in response to detecting an adverse impact of delivering fluid 102 to the recipient 108 as indicated by the feedback 175.

An adverse impact can be detected in a suitable manner. For example, in one embodiment, as previously discussed, the feedback 175 indicates current detected settings of the monitored one or more parameter. The algorithm 171 compares the current setting of the monitored setting to a first threshold value associated with the parameter. In one embodiment, if the current setting (such as respiration rate) is above the first threshold value, the algorithm 171 discontinues delivering the fluid 102 to the recipient 108 and sounds an alarm (audio and/or visual) to the caregiver 109.

In accordance with another embodiment, if the current setting of the monitored parameter (such as respiration rate) is below a respective second threshold value, the algorithm 171 discontinues delivering the fluid 102 to the recipient 108 and sounds an alarm (audio and/or visual) to the caregiver.

Accordingly, embodiments herein include modifying a delivery routine of delivering the particular fluid 102 to the recipient 108 based on comparison of the feedback 175 to corresponding one or more parameter threshold value settings associated with the algorithm 170-2.

If desired, the caregiver 109 can modify the settings of the threshold values during an operation of programming the fluid pump 120 with algorithm 170-2.

Figure 9:
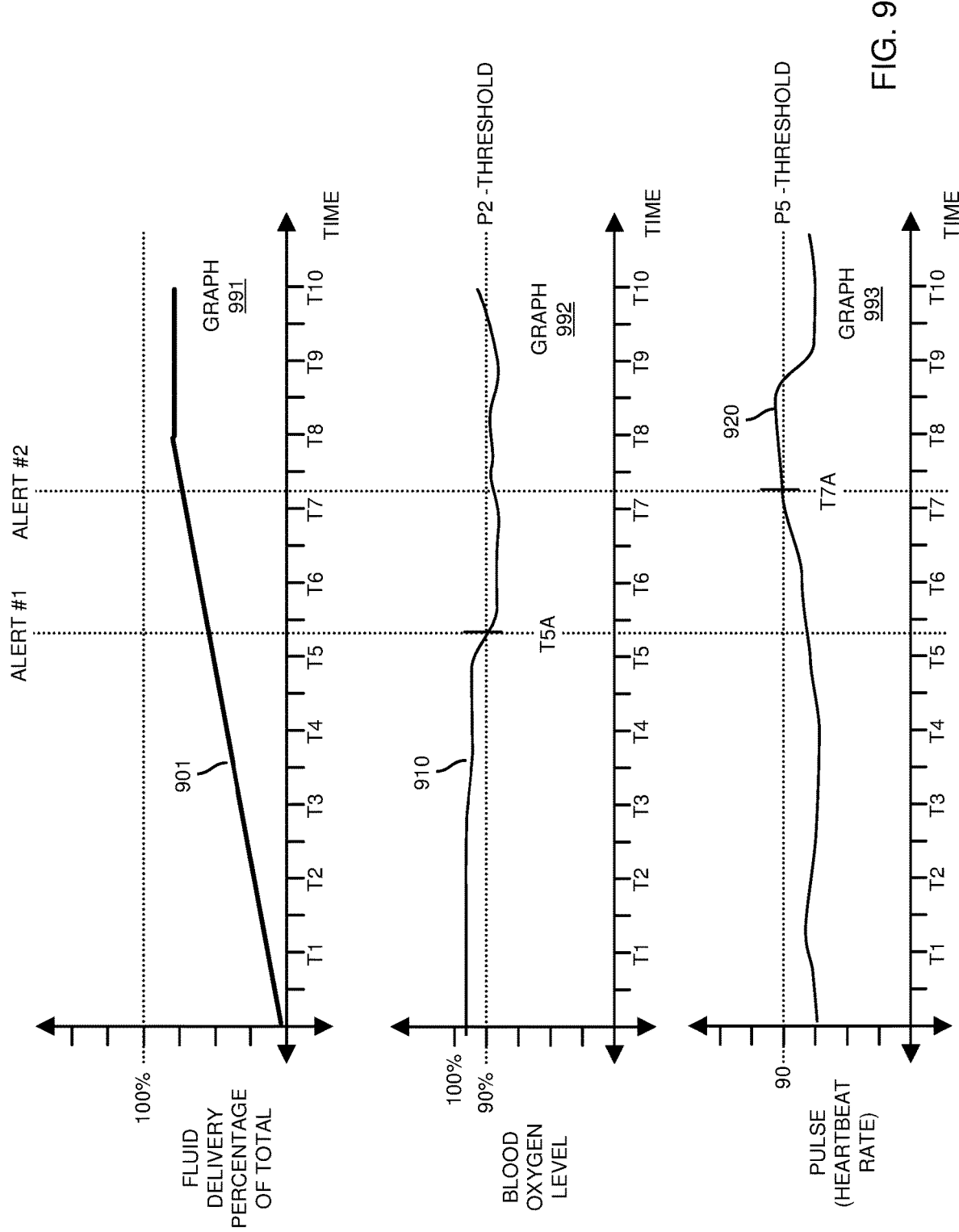
FIG. 9 is an example diagram illustrating monitoring of the feedback during delivery of a respective infusion according to embodiments herein.

FIG. 9 is an example diagram illustrating monitoring of the feedback during delivery of a respective infusion according to embodiments herein.

In this example embodiment, the graph 991 includes signal 901 derived from feedback 176 and corresponding fluid delivery information 785 (such as fluid delivery information 785-1, 785-2, etc.). Signal 901 generated by the feedback analyzer 113 or other suitable entity represents a progress of the delivering fluid 102 as indicated by the fluid order 115 over time. In other words, signal 901 indicates a percentage of completing the respective infusion (fluid order 115) over time as indicated by the feedback 176.

In further example embodiments, note that the monitor equipment 410, fluid pump 120, and the fluid management system 110 are synchronized to the same clock such that the feedback analyzer 113 is able to correlate the received infusion data from fluid pump 120 to the settings of monitored parameters P2 and P5.

Further in this example embodiment, based on the received feedback 175 and corresponding parameter P2 monitor data provided by the monitor equipment 410, the feedback analyzer 113 produces/tracks P2-signal 910 in graph 992. In one embodiment, the P2-signal 910 represents a blood oxygen level associated with the recipient 108 over time during the infusion. The feedback analyzer 113 tracks and compares P2-signal 910 (as derived from P2-MON-DATA in feedback 175) indicating the blood oxygen level associated with monitored parameter P2 of recipient 108 to the P2-threshold level. In response to detecting that the signal 910 falls below the P2-threshold level as implemented by the algorithm 170-2 between T5 and T6 (such as at around time T5A), the feedback analyzer 113 generates a respective first alert (ALERT #1) to the caregiver 109 such as via communications over network 190 and display of a respective message on the display screen 130 or audio alert indicating that the blood oxygen level of the recipient 108 has fallen below the P2-threshold level during infusion. The caregiver 109 may decide to discontinue the infusion based on the received alert.

Further in this example embodiment, based on the received feedback 175 and corresponding P5 monitor data, the feedback analyzer 113 produces P5-signal in graph 993. The P5-signal represents a heartbeat rate (pulse) associated with the recipient 108 over time during the infusion. The feedback analyzer 113 tracks and compares P5-signal 920 (as derived from P5-MON-DATA) indicating heartbeat rate (pulse) associated with monitored parameter P5 of recipient 108 to threshold level P5-threshold level. In response to detecting that the signal 920 raises above the P5-threshold level (such as 90 beats per minute) as implemented by the algorithm 170-2 between T7 and T8 (such as at time T7A), the feedback analyzer 113 generates a respective second alert (ALERT #2) to the caregiver 109 such as via display of a respective message on the display screen 130 or audible alert indicating that the blood oxygen level of monitor P2 has fallen below the P2-threshold level. The caregiver 109 may decide to discontinue the infusion based on the received alerts.

Assume in this example embodiment that, at or around time T8, the caregiver 109 discontinues delivery of the infusion as indicated by the fluid order 115 in response to receiving the multiple alerts.

In further example embodiments, note that the feedback analyzer 113 can be configured to generate a respective control command in response to detecting one or more alerts (such as ALERT #1 and/or ALERT #2). In one embodiment, the command communicated to the fluid pump 120 terminates delivery of the infusion as specified by the fluid order 115.

Figure 10:
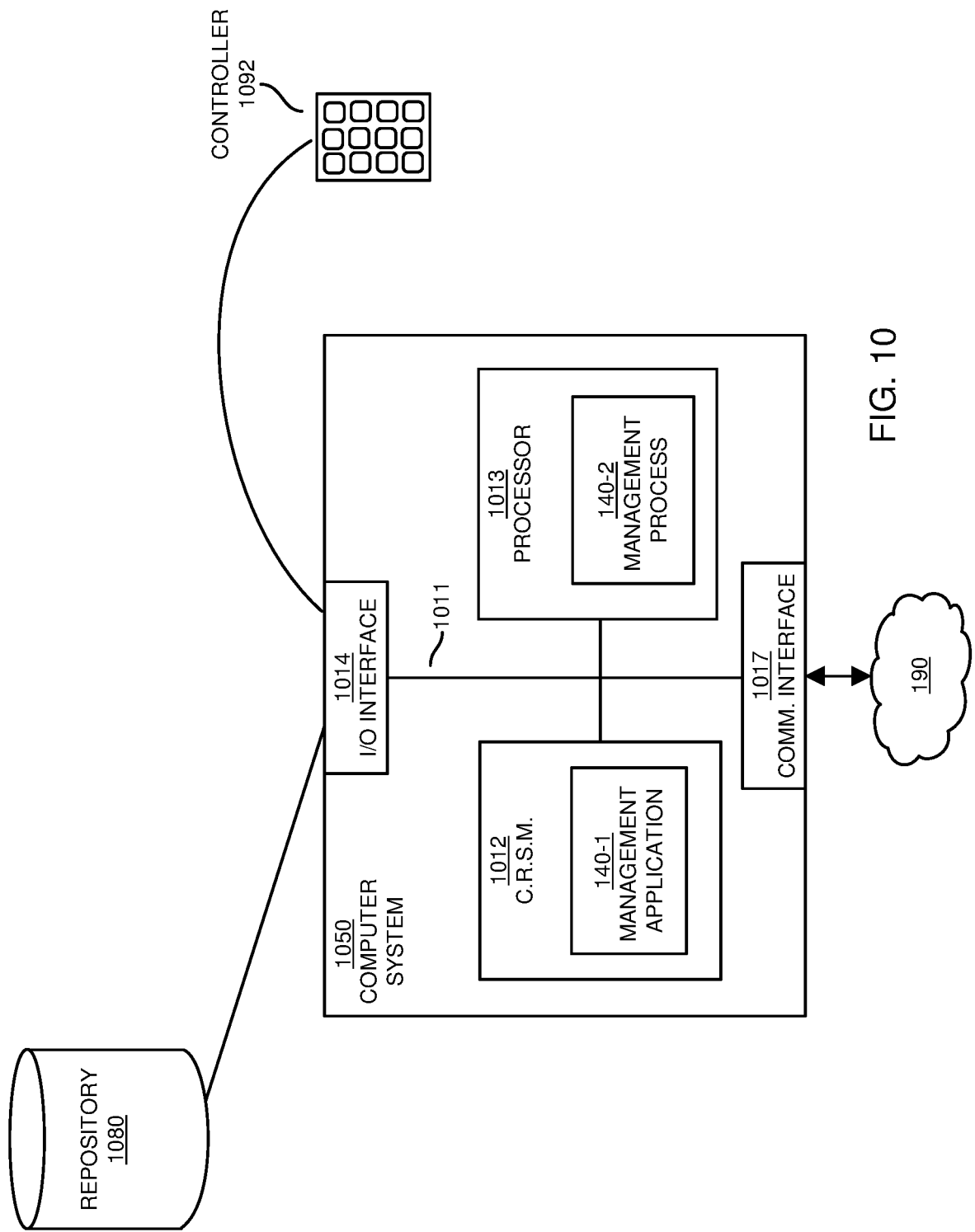
FIG. 10 is an example diagram illustrating a computer architecture in which to execute one or more embodiments as discussed herein.

FIG. 10 is an example block diagram of a computer device for implementing any of the operations as discussed herein according to embodiments herein.

In one embodiment, fluid management system 110 includes one or more computer systems similar to computer system 1050 to execute management application/process associated with the fluid management system 110, fluid pump manager 140, etc. As shown, computer system 1050 of the present example includes an interconnect 1011, a processor 1013 (such as one or more processor devices, computer processor hardware, etc.), computer readable storage medium 1012 (such as hardware storage to store data), I/O interface 1014, and communications interface 1017.

Interconnect 1011 provides connectivity amongst processor 1013, computer readable storage media 1012, I/O interface 1014, and communication interface 1017. I/O interface 1014 provides connectivity to a repository 1080 and, if present, other devices such as a playback device, display screen, input resource 1092, a computer mouse, etc.

Computer readable storage medium 1012 (such as a non-transitory hardware medium) can be any hardware storage resource or device such as memory, optical storage, hard drive, rotating disk, etc. In one embodiment, the computer readable storage medium 1012 stores instructions executed by processor 1013.

Communications interface 1017 enables the computer system 1050 and processor 1013 to communicate over a resource such as network 190 to retrieve information from remote sources and communicate with other computers. I/O interface 1014 enables processor 1013 to retrieve stored information from repository 1080.

As shown, computer readable storage media 1012 is encoded with controller application 140-1 (e.g., software, firmware, etc.) executed by processor 1013. Management application 140-1 can be configured to include instructions to implement any of the operations as discussed herein.

During operation of one embodiment, processor 1013 (e.g., computer processor hardware) accesses computer readable storage media 1012 via the use of interconnect 1011 in order to launch, run, execute, interpret or otherwise perform the instructions in management application 140-1 stored on computer readable storage medium 1012.

Execution of the management application 140-1 produces processing functionality such as management process 140-2 in processor 1013. In other words, the management process 140-2 associated with processor 1013 represents one or more aspects of executing management application 140-1 within or upon the processor 1013 in the computer system 1050.

Those skilled in the art will understand that the computer system 1050 can include other processes and/or software and hardware components, such as an operating system that controls allocation and use of hardware resources to execute management application 140-1.

In accordance with different embodiments, note that computer system may be any of various types of devices, including, but not limited to, a wireless access point, a mobile computer, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, or in general any type of computing or electronic device. In one non-limiting example embodiment, the computer system 1050 resides in fluid delivery system 100. However, note that computer system 1050 may reside at any location or can be included in any suitable one or more resources in network environment to implement functionality as discussed herein.

Functionality supported by the different resources will now be discussed via flowcharts in FIG. 11. Note that the steps in the flowcharts below can be executed in any suitable order.

Figure 11:
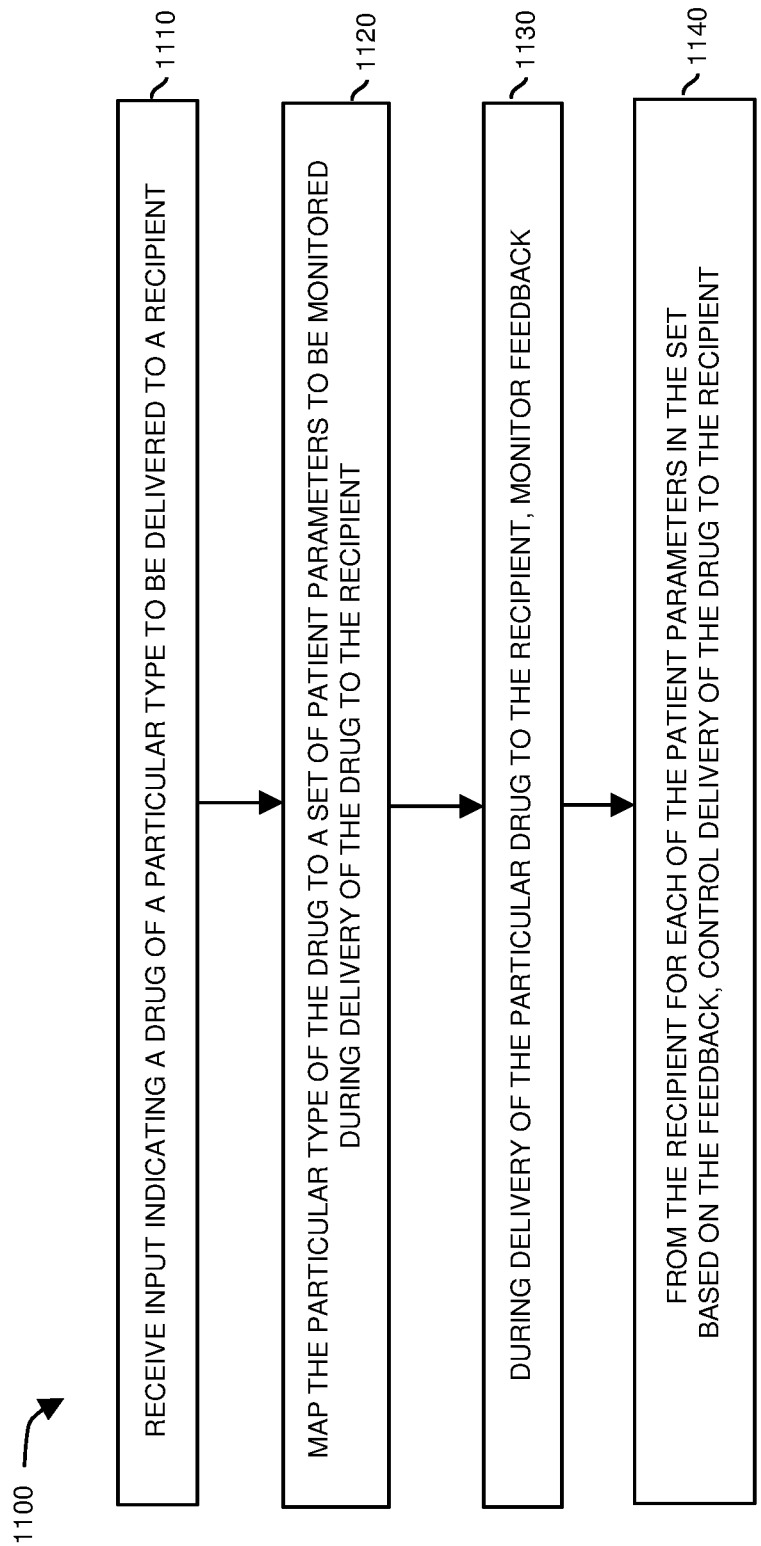
FIG. 11 is an example diagram illustrating a method according to embodiments herein.

FIG. 11 is a flowchart 1100 illustrating an example method according to embodiments. Note that there will be some overlap with respect to concepts as discussed above.

In processing operation 1110, the fluid management system 110 receives input such as a fluid order 115 indicating a fluid therapy of a particular type to be delivered to a recipient 108.

In processing operation 1120, the fluid management system 110 maps the particular type of the fluid (such as particular fluid type 2C) to a set of patient parameters (P2 and P5) to be monitored during delivery of the fluid 102 (fluid of particular type 2C) to the recipient 108.

In processing operation 1130, during delivery of the particular fluid typical 2C to the recipient 108, the fluid management system 110 monitors feedback 175 from the recipient 108 for each of the patient parameters P2 and P5 in the set.

In processing operation 1140, based on the feedback 175, the fluid management system 110 controls delivery of the particular type of fluid 2C (fluid 102) to the recipient 108.

Note again that techniques herein are well suited for use in management of fluid delivery systems. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A fluid management method to be implemented via processor-controlled fluid management hardware, the method comprising:
receiving, via one or more processors incorporated into the fluid management hardware, input indicating a fluid of a particular type to be delivered to a recipient;
in response to receiving the input indicating the fluid of the particular type, mapping, via the one or more processors, the fluid of the particular type to a set of parameters;
during the delivery of the fluid of the particular type to the recipient, monitoring, via the one or more processors, feedback from the recipient for each of the parameters in the set;
controlling, via the one or more processors, the delivery of the fluid of the particular type from a fluid pump to the recipient based on the feedback; and
wherein the method further includes: receiving threshold information associated with the set of parameters; performing a comparison of the monitored feedback to the threshold information; and based on the comparison, controlling the delivery of the fluid of the particular type from the fluid pump to the recipient.

2. The method as in claim 1, wherein the set of parameters are pertinent to the delivery of the fluid of the particular type and possible adverse effect to the recipient based on a history of delivering the fluid of the particular type to other recipients.

3. A system comprising:
fluid management hardware operative to:
receive input indicating a fluid of a particular type to be delivered to a recipient;
in response to receiving the input indicating the fluid of the particular type, map the fluid of the particular type to a first set of parameters;
during the delivery of the fluid of the particular type to the recipient, monitor feedback from the recipient for each of the parameters in the first set;
control the delivery of the fluid from a fluid pump to the recipient based on the feedback; and
wherein the fluid management hardware is further operative to: receive threshold information associated with the first set of parameters; perform a comparison of the monitored feedback to the threshold information; and based on the comparison, control the delivery of the fluid of the particular type from the fluid pump to the recipient.

4. The system as in claim 3, wherein the first set of parameters is pertinent to the delivery of the fluid of the particular type and possible adverse effect to the recipient based on a history of delivering the fluid of the particular type to other recipients.

5. The system as in claim 3, wherein the fluid management hardware is further operative to:
configure a fluid delivery algorithm of the fluid pump to monitor the feedback for the parameters in the first set; and
execute the fluid delivery algorithm at the fluid pump.

6. The system as in claim 3, wherein the fluid management hardware is operative to select the first set of parameters via mapping of the fluid of the particular type to the first set of parameters; and
wherein the fluid management hardware is further operative to: alert a caregiver during programming of the fluid pump regarding the first set of parameters to be monitored during the delivery of the fluid of the particular type to the recipient.

7. The system as in claim 3, wherein the fluid management hardware is further operative to:
discontinue the delivery of the fluid of the particular type from the fluid pump to the recipient in response to detecting an adverse impact to the recipient as indicated by the feedback.

8. The system as in claim 3, wherein the first set of parameters monitored via the feedback include lab results associated with the recipient.

9. The system as in claim 3, wherein the first set of parameters monitored via the feedback include vital signs of the recipient.

10. The system as in claim 9, wherein the vital signs include at least one of the following parameters:
i) heart rate,
ii) blood pressure,
iii) respiration rate,
iv) blood oxygen level,
v) blood glucose levels,
vi) partial thromboplastin time test, or
vii) cardiac output level.

11. The system as in claim 3, wherein the fluid management hardware is further operative to:
generate an alarm during the delivery of the fluid of the particular type from the fluid pump in response to detecting a condition associated with the delivery of the fluid as indicated by the feedback.

12. The system as in claim 3, wherein the first set of parameters pertinent to the delivery of the fluid of the particular type are learned from monitoring the delivery of the fluid of the particular type to a population of multiple patients and reactions of the multiple patients to receiving the fluid of the particular type.

13. The system as in claim 3, wherein the first set of parameters monitored via the feedback include assessments and clinical observations included in the recipient's record of care.

14. The system as in claim 3, wherein the fluid management hardware is operative to:
utilize map information to map the fluid of the particular type to the first set of parameters in response to receiving the input indicating the fluid of the particular type, the first set of parameters including a first parameter.

15. The system as in claim 14, wherein the fluid of the particular type is a first type of fluid, the map information mapping the first type of fluid to the first set of parameters; and
wherein the map information is operative to provide mapping of a second type of fluid to a second set of parameters.

16. The system as in claim 15, wherein the second set of parameters assigned to the second type of fluid specifies the first parameter and a second parameter.

17. The system as in claim 3, wherein the fluid management hardware is further operative to:
generate an alarm during the delivery of the fluid of the particular type from the fluid pump to the recipient in response to detecting a condition in which the feedback falls outside of a desired range during the delivery of the fluid of the particular type to the recipient.

18. The system as in claim 3, wherein the first set of parameters specifies a first parameter and a second parameter;
wherein the monitored feedback includes first feedback associated with the first parameter and second feedback associated with the second parameter;
wherein the fluid management hardware is operative to monitor the first feedback associated with the first parameter during the delivery of the fluid of the particular type to the recipient; and
wherein the fluid management hardware is operative to monitor the second feedback associated with the second parameter during the delivery of the fluid of the particular type to the recipient.

19. The system as in claim 18, wherein the fluid management hardware is further operative to:
generate a first alarm in response to detecting a first condition in which a magnitude of the first feedback crosses a first threshold level during the delivery of the fluid of the particular type to the recipient; and
generate a second alarm in response to detecting a second condition in which a magnitude of the second feedback crosses a second threshold level during the delivery of the fluid of the particular type to the recipient.

20. The system as in claim 3, wherein the recipient is a first recipient; and
wherein the first set of parameters are determined prior to the delivery of the fluid of the particular type to the first recipient, the first set of parameters determined based on a history of prior infusion of the fluid of the particular type to recipients other than the first recipient.

21. The system as in claim 3, wherein the first set of parameters is selected by the fluid management hardware, the first set of parameters selected from multiple sets of parameters.

22. Computer-readable storage hardware having instructions stored thereon, the instructions, when carried out by computer processor hardware, cause the computer processor hardware to:
receive input indicating a fluid of a particular type to be delivered to a recipient;
in response to receiving the input indicating the fluid of the particular type, map the fluid of the particular type to a first set of parameters;
during the delivery of the fluid of the particular type to the recipient, monitor feedback from the recipient for each of the parameters in the first set;
control the delivery of the fluid from a fluid pump to the recipient based on the feedback; and
wherein the computer processor hardware is further operative to: receive threshold information associated with the first set of parameters; perform a comparison of the monitored feedback to the threshold information; and based on the comparison, control the delivery of the fluid of the particular type from the fluid pump to the recipient.

* * * * *